(12) United States Patent
Okada et al.

(10) Patent No.: US 7,595,050 B2
(45) Date of Patent: Sep. 29, 2009

(54) HUMAN IGM MONOCLONAL ANTIBODY CAPABLE OF INDUCING APOPTOSIS IN HIV-INFECTED CELLS

(75) Inventors: Hidechika Okada, Nagoya (JP); Noriko Okada, Nagoya (JP)

(73) Assignee: Nagoya Industrial Science Research Institute, Aichi (JP)

( * ) Notice: Subject to any disclaimer, the term of this patent is extended or adjusted under 35 U.S.C. 154(b) by 345 days.

(21) Appl. No.: 10/519,855

(22) PCT Filed: Jun. 30, 2003

(86) PCT No.: PCT/JP03/08305

§ 371 (c)(1),
(2), (4) Date: Sep. 14, 2005

(87) PCT Pub. No.: WO2004/003021

PCT Pub. Date: Jan. 8, 2004

(65) Prior Publication Data

US 2006/0292160 A1    Dec. 28, 2006

(30) Foreign Application Priority Data

Jul. 1, 2002    (JP)    ............................. 2002-227953
Mar. 18, 2003    (JP)    ............................. 2003-074316

(51) Int. Cl.
*A61K 39/42*    (2006.01)

(52) U.S. Cl. .................................. 424/148.1

(58) Field of Classification Search ........................ None
See application file for complete search history.

(56) References Cited

FOREIGN PATENT DOCUMENTS

| EP | 0 510 691 A1 | 10/1992 |
|---|---|---|
| WO | WO97/22361 | 6/1997 |
| WO | WO00/18426 | 4/2000 |

OTHER PUBLICATIONS

N. Itoh et al., "The Polypeptide Encoded by the cDNA for Human Cell Surface Antigen Fas Can Mediate Apoptosis" Cell, vol. 66, No. 2, pp. 233-243, 1991.
Edited by Yoshihide Tsujimoto, Saishin Apoptosis Jikkenho (Separate vol. Experimental Medicine, Bio Manual UP Series), Mar. 25, 1997, pp. 112-117.
R. Klein et al., "Expressed Human immunogloblin k genes and their hypermutation", European Journal of Immunology, vol. 23, pp. 3248-3271, 1993.
X. Wang and B.D. Stollar, "Immunoglobulin VH Gene Expression in Human Aging", Clincial Immunology, vol. 93, No. 2, pp. 132-142, 1999.
TIA-1 "Cytotoxic cell" Marker, [online] Beckman Coutler Kabushiki Kaisha, 1999 [retrieved on Aug. 1, 2003], Internet, <URL:http://www.bc-cytometry.com/reagent/TIA-1.html>.

*Primary Examiner*—Jeffrey S. Parkin
(74) *Attorney, Agent, or Firm*—Sughrue Mion, PLLC

(57) ABSTRACT

A monoclonal antibody falling within the category of human IgM which specifically recognizes HIV-infected cells and induces apoptosis is obtained. Using the obtained antibody, it is intended to provide a remedy for patients suffering from HIV-infection, which contains as the active ingredient a human IgM antibody capable of specifically reacting with HIV-infected cells, inducing apoptosis in the infected cells and thus disrupting the cells, etc.

3 Claims, 5 Drawing Sheets

Schematic diagram of 2G9 μ-chain plasmid construct

HUMAN IGM MONOCLONAL ANTIBODY CAPABLE OF INDUCING APOPTOSIS IN HIV-INFECTED CELLS

TECHNICAL FIELD

The invention relates to a human IgM monoclonal antibody that specifically reacts with HIV-infected cells and induces apoptosis to the HIV-infected cells, and to a remedy for HIV-infection containing such antibody as an effective ingredient.

BACKGROUND ART

Various agents such as reverse transcriptase inhibitors and proteinase inhibitors have been developed for the treatment of HV-infection. Multidrug therapy using three to four kinds of these agents together (so-called highly active antiretroviral therapy: HAART) have been effective for HIV-infection patients to enable the blood HIV concentration to be remarkably reduced and the number of CD4 lymphocytes to be improved. However, HAART has been unable to eliminate latently infected cells and to completely cure the HIV-infected patients. Consequently, it has been a problem that HIV is revitalized in the latently infected cells and proliferate when medication is suspended.

While it has been reported that immunological response to the HIV is sometimes efficiently induced by intermittently repeating interruption and resuming of HAART, the method has not been recognized to be a reliable therapy. However, this result indicates the importance of the immunological response to HIV.

While human monoclonal antibodies that specifically react with the HIV-infected cells have been prepared by humanizing antibodies by gene recombination, they are IgG type antibodies. While the IgG antibody is a neutralizing antibody that inhibits HIV infections, it cannot impair infected cells.

While there are species-specific complement control membrane factors (such as DAF, decay accelerating factor; MCP, membrane cofactor protein; and HRF20, 20 kDa homologous restriction factor) on human cell membranes, they can induce no cytolysis reaction via complement reactions for preventing reactions among homologous human complements.

On the other hand, it was found that IgM antibodies in human serum that react with the HIV-infected cells are able to yield the cytolysis reaction of the HIV-infected cells via the human complement by overcoming the complement control membrane factors. It was revealed that the IgM antibody can exhibit such action as described above against gangliosides such as GM2 and Gg4 whose expression is enhanced by HIV-infection (Japanese Patent Application Laid-Open No. 9-227409, page 2, paragraph [0009]).

L55 has been reported as the human IgM monoclonal antibody against GM2 of the gangliosides, wherein L55 is produced by immortalizing human B lymphoblast strain with EB virus. The HIV-infected cells after treating with this human IgM monoclonal antibody have been found to yield cytolysis via a reaction with the human complement. However, since the L55 antibody is not specific to the HIV-infected cells, it may react with normal cells other than the HIV-infected cells.

DISCLOSURE OF INVENTION

An object of the invention is to provide a remedy for HIV-infected patients comprising human IgM antibody as an effective ingredient that specifically reacts with HIV-infected cells and induces apoptosis to the infected cells to lead the cells to destruction.

To solve the above problem, a first aspect of the invention is to provide a monoclonal antigen belonging to human IgM that specifically recognizes the HIV-infected cells and induces apoptosis to the cells.

A second aspect of the invention is to provide a remedy for HIV infection comprising human IgM antibody as an effective ingredient that specifically recognizes HIV-infected cells and induces apoptosis to the HIV-infected cells.

A third aspect of the invention is to provide the remedy according to the second aspect used for preventing onset of AIDS.

A fourth aspect of the invention is to provide the human IgM monoclonal antibody according to any of first to third aspects, wherein the human IgM monoclonal antibody that reacts with the HIV-infected cells is 2G9 antibody having a base sequence of the H-chain variable region represented by SEQ ID NO. 1.

A fifth aspect of the invention is to provide the human IgM monoclonal antibody according to any of first to fourth aspects, wherein the human IgM monoclonal antibody that reacts with the HIV-infected cells is 2G9 antibody having a base sequence of the L-chain variable region represented by SEQ ID NO. 2.

OM10.1 cells that are latently infected cells react with 2G9 antibodies while they do not react with antibodies (0.5β) against gp120 as a membrane protein antigen against HIV.

Figure 3:
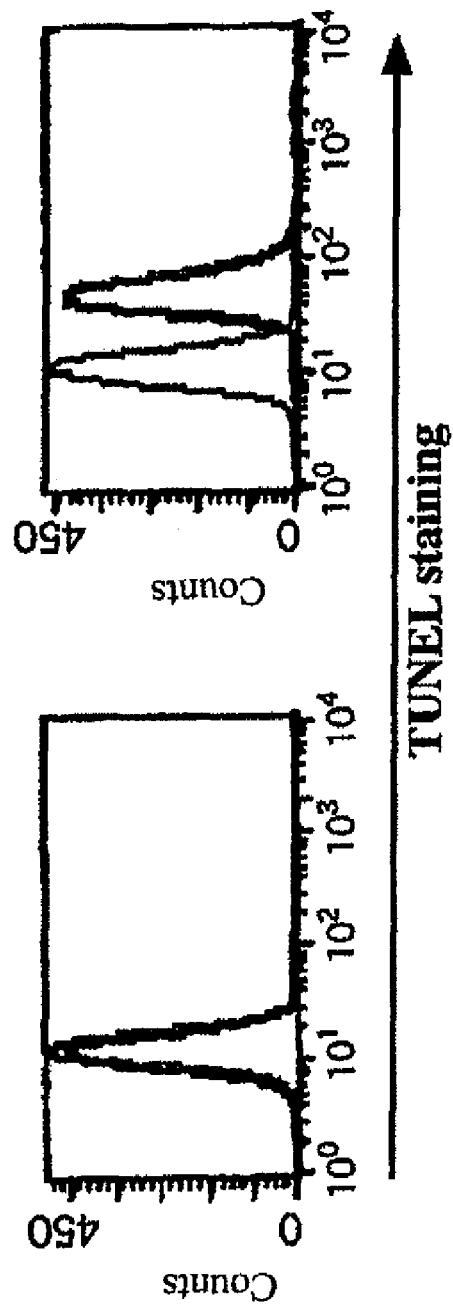

FIG. 3 shows apoptosis of HIV-infected cells with 2G9 antibody.

It shows that MOLT-4/IIIB cells infected with HIV is completely stained with an apoptosis detection reagent by TUNEL method after MOLT-4/IIIB cells are cultivated for 2 days by adding 2G9 antibody to the culture in a concentration of 50 μg/ml. Non-infected MOLT-4 cells are not affected at all.

Figure 4:
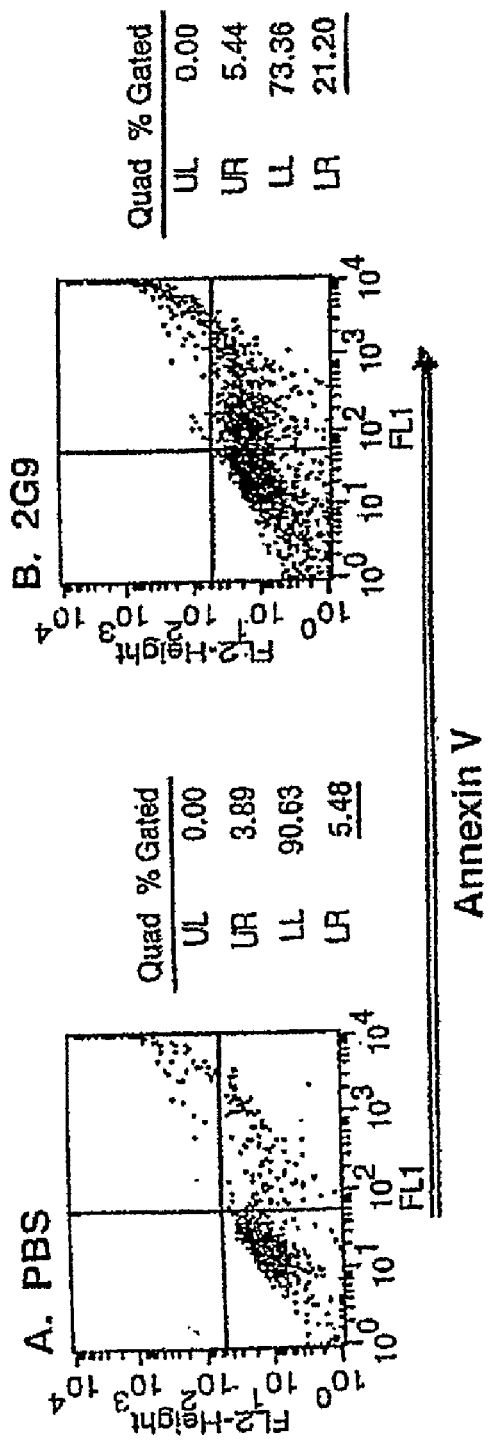

FIG. 4 shows apoptosis of HIV latently infected cells with 2G9 antibodies.

It shows that when 2G9 antibody is added to HIV-infected OM10.1 cells in a concentration of 12.5 μg/ml and the cells are cultivated for 2 days, the proportion of cells that react with Annexin V as an apoptosis detection reagent increases from 5.5% to 21.2% as compared with the proportion when no antibody is added.

Figure 5:
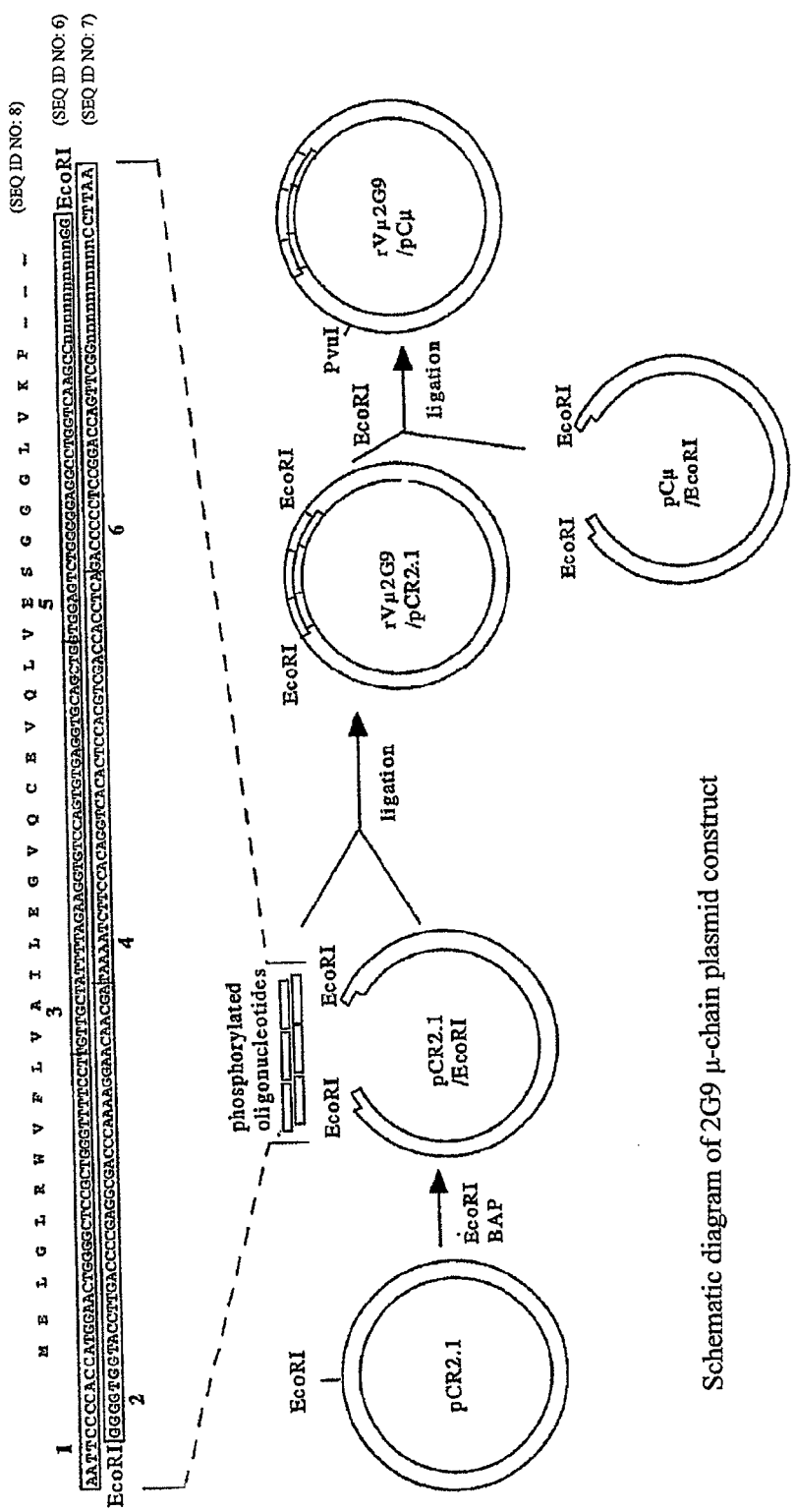

FIG. 5 schematically illustrates 2G9μ chain expression plasmid construct.

BEST MODE FOR CARRYING OUT THE INVENTION

While the invention is described in detail with reference to examples, the technical scope of the invention is by no means restricted to these examples.

For solving the problems above, the inventors of the invention immunized HIV-infected cells of a mouse (TC mouse: trans-chromosome mouse; prepared by Kirin Brewery Co., Ltd.) into which human immunoglobulin gene-containing chromosomes had been introduced, and obtained a mouse that produces human antibodies that specifically react with HIV-infected cells. Hybridomas were prepared by a conventional method by allowing spleen cells of immunized mouse to fuse with mouse myeloma cell strain. Clones that produce monoclonal antibodies that react with HIV infection cells are selected from the hybridomas obtained, and the selected hybridomas were named as 2G9 cell strain. A 2G9 antibody that is a monoclonal antibody produced by 2G9 cell strain is a human IgM monoclonal antibody comprising human μ-chain and human κ-chain. While the 2G9 antibody specifically reacts with HIV-infected cells, it can also reacts with latently infected cell strain OM10.1. The invention have been completed by confirming that these cells are destroyed by inducing apoptosis. The cell strain 2G9 that produces 2G9 antibodies of the invention was deposited with National Institute of Advanced Industrial Science and Technology, International Patent Organism Depository (Chuo-6, Higashi 1-1-1, Tsukuba City, Ibaraki Pref.), on May 8, 2003, with an accession number of FERM BP-8378.

The antigen (2G9 antigen) that reacts with 2G9 antibody is considered to lose its reactivity with 2G9 antibody by treating with SDS.

Table 1 shows the results of base sequence analysis of the genes in the variable regions in κ-chain and μ-chain, respectively, encoding 2G9 antibody. The base sequence of the constant region is approximately the same as the base sequence of reported genes.

TABLE 1

SEQ ID NO.: 1
Base Sequence of μ-Chain Variable Region
TGCCCTGGATTCCAAGGCCTATCCACTTGGTGATCAGCACTGAGCACCGAG

GATTCACCATGGAACTGGGGCTCCGCTGGGTTTTCCTTGTTGCTATTTTAG

AAGGTGTCCAGTGTGAGGTGCAGCTGGTGGAGTCTGGGGGAGGCCTGGTCA

AGCCTGGGGGGTCCCTGAGACTCTCCTGTGCAGCCTCTGGATTCACCTTCA

GTACTTATAGCATGAACTGGGTCCGCCAGGCTCCAGGGAAGGGGCTGGAGT

GGGTCTCATCCATTAGTAGTAGTAGTAGTTACATATACTACGCAGACTCAG

TGAAGGGCCGATTCACCATCTCCAGAGACAACGCCAAGAACTCACTGTATC

TGCAAATGAACAGCCTGAGAGCCGAGGACACGGCTGTGTATTACTGTGCGA

GAGATCTCCTTATAGCAGTGGCTGGCCACTGGGGCCAGGGAACCCTGGTCA

CCGTCTCCTCA

SEQ ID NO.: 2
Base Sequence of κ-Chain Variable Region
CTCAGTCAGGACACAGCATGGACATGAGGGTCCCTGCTCAGCTCCTGGGAC

TCCTGCTGCTCTGGCTCCCAGATACCAGATGTGACATCCAGATGACCCAGT

CTCCATCCTCCCTGTCTGCATCTGTAGGAGACAGAGTCACCATCACTTGCC

GGGCGAGTCAGGGCATTAGCAATTATTTAGCCTGGTATCAGCAGAAACCAG

GGAAAGTTCCTAAACTCCTGATCTATGCTGCATCCACTTTGCAATCAGGGG

TCCCATCTCGGTTCAGCGGCAGTGGATCTGGGACAGATTTCACTCTCACCA

TCAGCAGCCTGCAGCCTGAAGATGTTGCAACTTATTACTGTCAAAAGTATA

ACAGTGCCCCGTACACTTTTGGCCAGGGGACCAAGCTGGAGATCAAA

Table 1

Base Sequence of μ-Chain Variable Region

Base Sequence of κ-Chain Variable Region

The antibody according to the first aspect, for example 2G9 antibody, is able to induce apoptosis to HIV-infected cells including OM10.1 cells. In other words, this antibody is IgM monoclonal antibody capable of specifically inducing apoptosis to the HIV-infected cells. Since the antibody is also able to induce apoptosis to HIV latently infected cells such as OM10.1 cells, it can be used as a remedy for eliminating HIV latent infection lurking in HIV-infected patient's body in which chemotherapeutic agents cannot exhibit their effects.

The therapeutic agent of the invention utilized as a remedy of HIV-infected patients comprising human IgM antibody as an effective ingredient, which induces apoptosis to the HIV-infected cells to lead them to destruction by specifically reacting with the HIV-infected cells, can be obtained by combining the agent with a physiologically acceptable carrier. The physiologically acceptable carrier is known in the art, and includes physiological buffered saline or other aqueous solutions having a buffer action, or solvents such as glycols, glycerol oils (for example olive oil) or injectable organic esters. The physiologically acceptable carrier may include compounds that stabilize IgM antibody or enhance absorption thereof. Examples of the physiologically acceptable compounds include sugars such as glucose, sucrose and dextran; antioxidants such as ascorbic acid and glutathione; chelating agents; proteins such as albumin; and other stabilizers and excipients. Other physiologically active substances such as transcriptase inhibitors and protease inhibitors may be further added. Any combinations of the physiologically acceptable carriers may be selected depending on administration path and disease of object.

Example 1

Specificity of 2G9 Antibody

Figure 1:
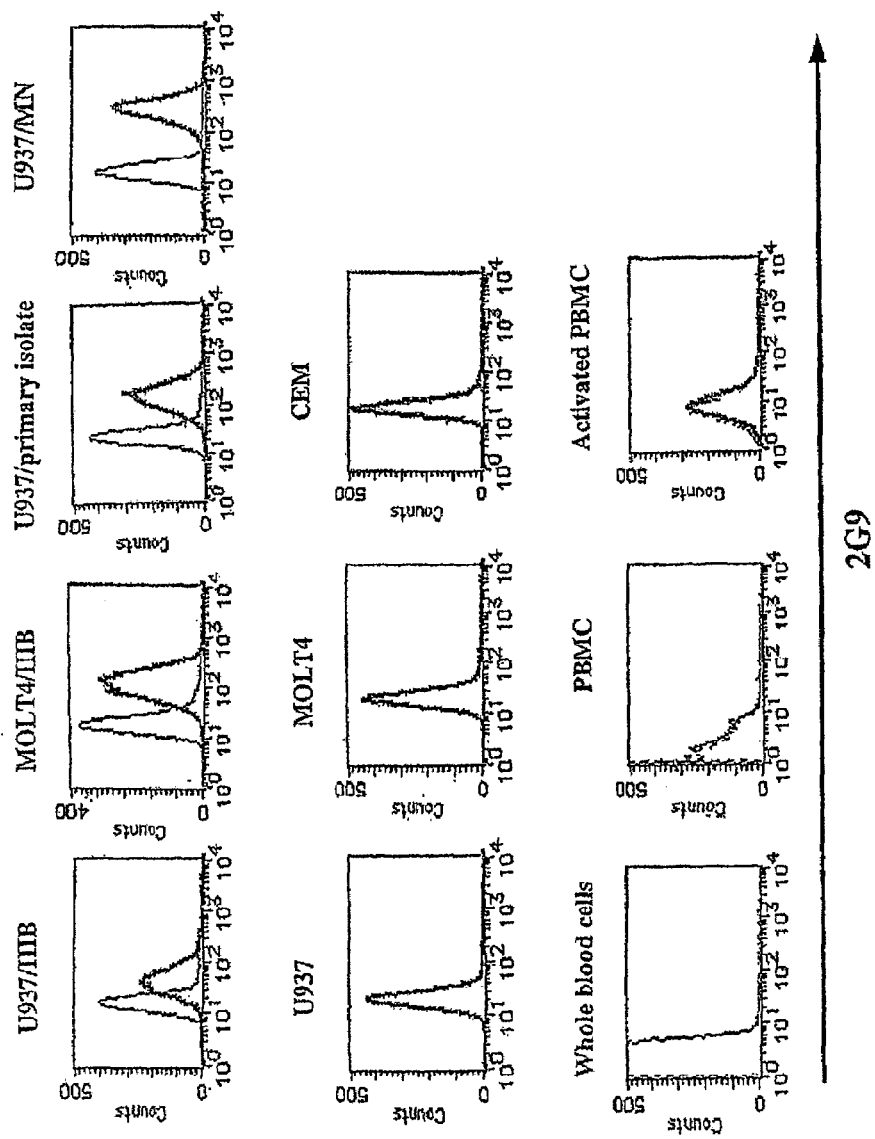
FIG. 1 shows specificity of 2G9 antibody. The result of flow cytometry analysis shows that HIV-infected cells are stained with 2G9 antibodies while non-infected cells are not (PBMC: peripheral blood lymphocyte; IIIB, primary isolate and MN denote the names of HIV).
Figure 2:
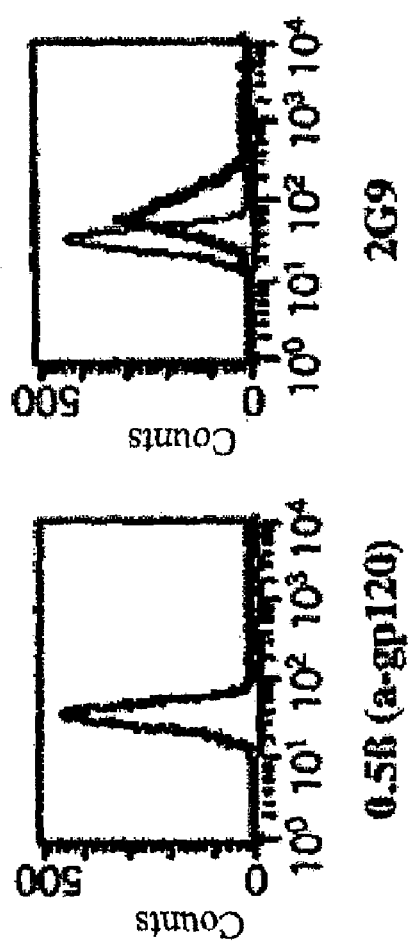
FIG. 2 shows that 2G9 antibodies also react with HIV latently infected cells.

Reactivity of 2G9 antibody against the HIV-infected cells was analyzed by flow cytometery. U937 cells, MOLT-4 cells and CEM cells as cultured cell strains were used as the cells to be tested. The HIV-infected cells used were U937/IIIB prepared by infecting U937 cells with IIIB strain of HIV-1, U937/orimary isolate infected with primary isolate mono strain, U937/MIN infected with MN strain, and MOLT-4/IIIB prepared by infecting MOLT-4 with IIIB strain. After washing the cells treated with 2G9 antibody, the cells were stained with anti-human IgM antibody labeled with a fluorescent pigment, and the fluorescence intensity of the cells was analyzed by flow cytometery. The results showed that, while U937/IIIB, U937/primary isolate, U937/MIN and MOLT-4/IIIB of the HIV-infected cells were strongly stained with 2G9 antibody, non-infected MOLT-4 cells and CEM cells were not stained at all. The results of analysis of peripheral blood lymphocytes of normal adults and activated lymphocytes prepared by cultivating the peripheral blood lymphocytes for 3 days after stimulating with phyto-hemagglutinin (PHA) showed that these cells do not react with 2G9 antibody at all. Accordingly, it was revealed that, while 2G9 antibody specifically reacts with HIV-infected cells, the antigen does not react with normal cells (FIG. 1). OM10.1 cells are considered to be a HIV latently infected cell strain, and usually do not express antibodies against HIV such as gp120. However, since 2G9 antibody reacts with OM10.1 cells, it was revealed that 2G9 antibody is able to react with cells in a latent infection phase (FIG. 2).

Example 2

Apoptosis of HIV-Infected Cells with 2G9 Antibody

MOLT-4/IIIB cells infected with HIV-1 were seeded in RPMI1640 culture medium supplemented with 20% of inactivated human serum in a concentration of $5 \times 10^5$ cells/ml, and the cells were cultivated in an incubator containing 5% of carbon dioxide at 37° C. for 2 days by adding an equal volume of 100 μg/ml 2G9 antibody solution. DNA fragmentation as an index of apoptosis was stained by TUNEL method after the culture, followed by flow cytometory analysis by fixing the cells with 1% paraformaldehyde. As shown in FIG. 3, while the cells were not stained when the cells were not treated with 2G9 antibody, the cells were completely stained after cultivating in the presence of 2G9 antibody. This result indicates that 2G9 antibody has an action for inducing apoptosis to infected cells. No such impairing action was observed in non-infected MOLT-4 cells (FIG. 3).

Example 3

Apoptosis of HIV Latently Infected Cells with 2G9 Antibody

OM10.1 cells as the latently infected cell strain were seeded in a concentration of 1×10⁵ cells/ml in a cell culture medium (RPMI1640 medium) containing 20% of inactivated human serum, and an equal volume of a 2G9 antibody solution in a concentration of 12.5 μg/ml was added to the culture followed by cultivation at 37° C. for 2 days. The cells after the culture were stained with Annexin V as an apoptosis detection agent, and the cells were fixed with 1% paraformaldehyde for analysis by flow cytometry. The results in FIG. 4 shows that, while 5.5% of the cells were stained when not treated with 2G9 antibody, 21.2% of the cells were stained when cultured in the presence of 2G9 antibody. It was therefore confirmed that 2G9 antibody also has an action for inducing apoptosis to OM10.1 cells of HIV-latent infection cells.

Example 4

Reconstruction of Antibody by Gene Engineering

An example of the method for reconstruction of 2G9 antibody based on the base sequence of the variable region of 2G9 antibody shown in TABLE 1 will be described below, wherein 2G9 antibody-producing cell strains were established using gene engineering such as a shot-gun ligation method (Grundstrom, T. et al., Nucleic Acid Res. 13, 3305-3316, 1985).

Amino acid sequences of the variable region of 2G9 antibody were obtained by translating the base sequence in the table. There are many base sequences encoding the amino acid sequences in the variable region of 2G9 antibody as shown in Table 2, such as the base sequence of the variable region of original 2G9 antibody as well as those obtained by changing used codons. Base sequences having certain kinds of restriction enzyme recognition fragment were selected from the sequences for every length capable of chemically synthesizing as oligonucleotides (Table 2).

TABLE 2: Examples of cDNA, and equivalent amino acids (i.e., SEQ ID NOs: 4 and 5 and conservatively modified variants thereof), encoding the amino acid sequence of 2G9 antibody (SEQ ID NO: 3)

```
              1
SEQ ID NO: 3  M    E    L    G    L    R    W    V    F    L    V    A    I    L    E    F    V    Q    C    E
SEQ ID NO: 4  ATA  GAA  TTA  GGT  TTA  CGT  TGA  GTT  TTT  TTA  GTT  GCT  ATT  TTA  GAA  GGT  GTT  CAA  TGT  GAA
SEQ ID NO: 5  ATG  GAG  TTG  GGC  TTG  CGC  TGG  GTC  TTC  TTG  GTC  GCC  ATC  TTG  GAG  GGC  GTC  CAG  TGC  GAG
                        CCT  GGA  CCT  CGA       GTA       CTT  GTA  GCA       CTT       GGA  GTA
                        CTC  GGG  CTC  CGG       GTG       CTC  GTG  GCG       CTC       GGG  GTG
                        CTA            CTA                 CTA                 CTA
                        CTG            CTG                 CTG                 CTG

21
              V    Q    L    V    E    S    G    G    G    L    V    K    R    G    S    L    R    K    S
              GTT  CAA  TTA  GTT  GAA  TCT  GGT  GGT  GGT  TTA  GTT  AAA  CCT  GGT  GGT  TCT  TTA  CGT  TTA  TCT
              GTC  CAG  TTG  GTC  GAG  TCC  GGC  GGC  GGC  TGG  GTC  AAG  CCC  GGC  GGC  TCC  TTG  CGC  TTG  TCC
              GTA       CTT  GTA       TCA  GGA  GGA  GGA  CTT  GTA       CCA  GGA  GGA  TCA  CTT  CGA  CTT  TCA
              GTG       CTC  GTG       TCG  GGG  GGG  GGG  CTC  GTG       CCG  GGG  GGG  TCG  CTC  CGG  CTC  TCG
                        CTA            AGT                 CTA                           AGT  CTA       CTA  AGT
                        CTG            AGC                 CTG                           AGC  CTG       VTG  AGC

41
              C    A    A    S    G    F    T    F    S    T    Y    S    M    N    W    V    R    Q    A    P
              TGT  GCT  GCT  TCT  GGT  TTT  ACT  TTT  TCT  ACT  TAT  TCT  ATA  AAT  TGA  GTT  CGT  CAA  GCT  CCT
              TGC  GCC  GCC  TCC  GGC  TTC  ACC  TTC  TCC  ACC  TAC  TCC  ATG  AAC  TGG  GTC  CGC  CAG  GCC  CCC
                   GCA  GCA  TCA  GGA       ACA       TCA  ACA       TCA                 GTA  CGA       GCA  CCA
                   GCG  GCG  TCG  GGG       ACG       TCG  ACG       TCG                 GTG  CGG       GCG  CCG
                                  AGT                      AGT            AGT
                                  AGC                      AGC            AGC

61
              G    K    G    L    E    W    V    S    S    I    S    S    S    S    S    Y    I    Y    Y    A
              GGT  AAA  GGT  TTA  GAA  TGA  GTT  TCT  TCT  ATT  TCT  TCT  TCT  TCT  TCT  TAT  ATT  TAT  TAT  GCT
              GGC  AAG  GGC  TTG  GAG  TGG  GTC  TCC  TCC  ATC  TCC  TCC  TCC  TCC  TCC  TAC  ATC  TAC  TAC  GCC
              GGA       GGA  CTT       TGG       TCA  TCA       TCA  TCA  TCA  TCA  TCA                      GCA
              GGG       GGG  CTC            TCT  TCG  TCG       TCG  TCG  TCG  TCG  TCG                      GCG
                             CTA                      AGT  AGT       AGT  AGT  AGT  AGT  AGT
                             CTG                      AGC  AGC       AGC  AGC  AGC  AGC  AGC

81
              D    S    V    K    G    R    F    T    I    S    R    D    N    A    K    N    S    L    T    L
              GAT  TCT  GTT  AAA  GGT  CGT  TTT  ACT  ATT  TCT  CGT  GAT  AAT  GCT  AAA  AAT  TCT  TTA  TAT  TTA
              GAC  TCC  GTC  AAG  GGC  CGC  TTC  ACC  ATC  TCC  CGC  GAC  AAC  GCC  AAG  AAC  TCC  TTG  GAC  TTG
                   TCA  GTA       GGA  CGA       ACA       TCA  CGA       GCA            TCA  CTT       CTT
                   TCG  GTG       GGG  CGG       ACG       TCG  CGG       GCG            TCG  CTC       CTC
                   AGT                                     AGT                                AGT  CTA       CTA
                   AGC                                     AGC                                AGC  CTG       CTG
```

Oligonucleotides were chemically synthesized based on the base sequence divided for each restriction enzyme-recognition fragment. After sequentially digesting the synthesized oligonucleotide with a corresponding restriction enzyme, a full length of a base sequence encoding the amino acid sequence of the 2G9 antibody variable region by ligation was obtained. cDNA fragments of the 2G9 antibody variable regions of the H-chain and L-chain obtained by the same method with each other (named as rVµ2G9 and rVκ2H9, respectively) were integrated into vectors having constant region gene sequences of H-chain and L-chain of the human IgM antibody (Cµ and Cκ, respectively) by the same method as forming chimera antibodies to obtain recombinant 2G9µ-chain and κ-chain expression plasmids (rVµ2G9-Cµ and rVκ2G9-Cκ, respectively; FIG. 5).

Example 5

Expression of Recombinant Antibody

Activities of the antibodies obtained using the plasmids expressing the reconstructed 2G9 antibody genes were investigated with a temporary expression system in COS7 cells (ATCC CRL 1651). Genes were introduced using a mixture of two plasmids (rVµ2G9-Cµ and rVκ2G9-Cκ) and an expression plasmid (Cj) for J-chain of human IgM antibody using a lipofectamine reagent according to the protocol by GIBCO Co. Cultivation was continued for two days thereafter under a usual culture condition, and the supernatant of the gene-introduced cell culture was retrieved. Recombinant 2G9 antibodies secreted in the culture supernatant were confirmed by subjecting the culture supernatant to an assay system by the sandwich ELISA method using antihuman µ-antibody and antihuman κ-antibody. The antibodies were confirmed to have specificity as described above by FACS analysis of the culture supernatant using cells such as U937/IIIB and MOLT-4/IIIB prepared by infection of U937 cells and MOLT-4 with IIIB strain of HIV-1. Further, the activity of recombinant 2G9 antibody was confirmed by a competitive inhibition test by allowing fluorescence-labeled original 2G9 antigen and the culture supernatant to simultaneously react with U937/IIIB or MOLT-4/IIIB.

Consequently, it was confirmed that the base sequences of the µ-chain and κ-chain variable regions of 2G9 antibody listed in Table 1 are quite important regions responsible for anti-HIV activities.

It was also confirmed from these results that genes encoding the base sequences of the µ-chain variable region and κ-chain variable region are quite crucial genes for preparing the recombinant anti-HIV antibody.

INDUSTRIAL APPLICABILITY

2G9 antibody obtained in the invention was recognized to have an apoptosis-inducing action against OM10.1 cells of the latently infected cells. 2G9 antibody was also recognized to have the apoptosis-inducing action against infected cells. On the contrary, the antibody did not impair U937 and MOLT-4 cells as non-infected cells. These results show that 2G9 antibody of the invention can be used as a remedy for eliminating latent infection lurking in the body of infected patients to whom chemotherapy is ineffective, since the antibody is able to induce apoptosis to latently infected cells. The invention also provides genes encoding the base sequences of the µ-chain variable region and κ-chain variable regions that are quite crucial for preparing the recombinant anti-HIV antibody.

The invention claimed is:

1. A human IgM monoclonal antibody which induces apoptosis of HIV-infected cells upon binding to said cells, wherein said antibody comprises a heavy-chain variable region encoded by a polynucleotide comprising the nucleotide sequence of SEQ ID NO: 1 and a light-chain variable region encoded by a polynucleotide comprising the nucleotide sequence of SEQ ID NO: 2.

2. The antibody of claim 1, wherein said antibody is produced by the hybridoma deposited under Accession No. FERM BP-8378.

3. A composition comprising the antibody of claim 1 or 2 and a pharmaceutically acceptable carrier.

* * * * *

SEQUENCE LISTING

```
<160> NUMBER OF SEQ ID NOS: 2

<210> SEQ ID NO 1
<211> LENGTH: 470
<212> TYPE: DNA
<213> ORGANISM: Unknown
<220> FEATURE:
<223> OTHER INFORMATION: variable region of human fE-chain
<220> FEATURE:
<221> NAME/KEY: V-region
<222> LOCATION: (1)..(470)
<223> OTHER INFORMATION:

<400> SEQUENCE: 1
tgccctggat tccaaggcct atccacttgg tgatcagcac tgagcaccga ggattcacca      60
tggaactggg gctccgctgg gtttccttg ttgctatttt agaaggtgtc cagtgtgagg     120
tgcagctggt ggagtctggg ggaggcctgg tcaagcctgg ggggtccctg agactctcct     180
gtgcagcctc tggattcacc ttcagtactt atagcatgaa ctgggtccgc caggctccag     240
ggaaggggct ggagtgggtc tcatccatta gtagtagtag tagttacata tactacgcag     300
actcagtgaa gggccgattc accatctcca gagacaacgc caagaactca ctgtatctgc     360
aaatgaacag cctgagagcc gaggacacgg ctgtgtatta ctgtgcgaga gatctcctta     420
tagcagtggc tggccactgg ggccagggaa ccctggtcac cgtctcctca                470
```

```
<210> SEQ ID NO 2
<211> LENGTH: 404
<212> TYPE: DNA
<213> ORGANISM: Unknown
<220> FEATURE:
<223> OTHER INFORMATION: variable region of human k-chain
<220> FEATURE:
<221> NAME/KEY: V-region
<222> LOCATION: (1)..(404)
<223> OTHER INFORMATION:

<400> SEQUENCE: 2
ctcagtcagg acacagcatg gacatgaggg tccctgctca gctcctggga ctcctgctgc      60
tctggctccc agataccaga tgtgacatcc agatgaccca gtctccatcc tccctgtctg     120
catctgtagg agacagagtc accatcactt gccgggcgag tcagggcatt agcaattatt     180
tagcctggta tcagcagaaa ccagggaaag ttcctaaact cctgatctat gctgcatcca     240
ctttgcaatc aggggtccca tctcggttca gcggcagtgg atctgggaca gatttcactc     300
tcaccatcag cagcctgcag cctgaagatg ttgcaactta ttactgtcaa aagtataaca     360
gtgccccgta cacttttggc caggggacca agctggagat caaa                     404
```